United States Patent [19]

Esders

[11] 4,322,496
[45] Mar. 30, 1982

[54] INHIBITION OF LACTATE OXIDASE

[75] Inventor: Theodore W. Esders, Webster, N.Y.

[73] Assignee: Eastman Kodak Company, Rochester, N.Y.

[21] Appl. No.: 141,026

[22] Filed: Apr. 17, 1980

[51] Int. Cl.$^3$ .......................... C12Q 1/26; C12N 9/99
[52] U.S. Cl. ........................................ 435/25; 435/28; 435/184; 435/190; 435/805
[58] Field of Search ...................... 435/4, 25, 28, 184, 435/189, 190, 805

[56] References Cited

U.S. PATENT DOCUMENTS

| | | | |
|---|---|---|---|
| 3,703,591 | 11/1972 | Bucolo et al. | 435/15 |
| 3,759,793 | 9/1973 | Stork et al. | 435/55 |
| 3,862,009 | 1/1975 | Wahlefeld et al. | 435/26 |
| 3,898,130 | 8/1975 | Komatsu | 435/19 |
| 3,956,069 | 5/1976 | Allain et al. | 435/14 |
| 4,012,287 | 3/1977 | Carl et al. | 435/26 |
| 4,166,005 | 8/1979 | Masurekan et al. | 435/190 |
| 4,237,222 | 12/1980 | Misaki et al. | 435/25 |
| 4,241,178 | 12/1980 | Esders et al. | 435/28 |

FOREIGN PATENT DOCUMENTS 7413057 4/1975 Netherlands.

OTHER PUBLICATIONS

Ghisla et al., "Mechanism of Inactivation of the Flavoenzyme Lactate Oxidase by Oxalate", *J. Biol. Chem.*, vol. 250, No. 2, (1975), pp. 577-584.

Ghisla et al., "Studies on the Mechanism of Action of the Flavoenzyme Lactate Oxidase", *J. Biol. Chem.*, vol. 252, No. 19, (1977), pp. 6729-6735.

Barman, *Enzyme Handbook*, vol. 1, Springer-Verlag, New York Inc., N.Y., (1969), p. 111.

*Primary Examiner*—Thomas Wiseman
*Attorney, Agent, or Firm*—J. Jeffrey Hawley

[57] ABSTRACT

Inhibition of lactate oxidase and an enzymatic analysis of an aqueous liquid containing lactate or lactic acid for an analyte other than lactate or lactic acid are disclosed. Undesired lactate oxidase activity, if any, in an enzymatic reagent composition, is inhibited by a lactate oxidase inhibitor selected from glyoxalic acid, oxalic acid, glycolic acid, and salts thereof. Preferred enzymatic analyses are performed in the presence of a lactate oxidase inhibitor with an enzymatic reagent composition producing hydrogen peroxide as a detectable species.

13 Claims, No Drawings

INHIBITION OF LACTATE OXIDASE

FIELD OF THE INVENTION

The present invention relates to the inhibition of lactate oxidase and to enzymatic analyses of aqueous liquids in which the inhibition of any lactate oxidase present eliminates or substantially reduces lactic acid or lactate interference with the analysis.

BACKGROUND OF THE INVENTION

The analysis of aqueous liquids to determine the presence or concentration of one or more components of the liquid, hereinafter designated analyte(s), is extremely important. Such analyses are carried out in a wide variety of situations including, among others, analyses of aqueous industrial liquids and analyses of aqueous liquids of biological origin such as are performed in hundreds of doctors' offices, clinics, and hospitals each day. Increasing numbers of these analyses are now being performed in whole or in part, by use of enzymatic reagents. For example, the use of glucose oxidase in serum glucose tests has become widely accepted as a standard method for determination of serum glucose.

Many of the enzymatic reagents used in these various liquid analysis procedures are derived from microbiological organisms. Although many, if not most, of these enzymatic reagents are highly specific in terms of their "catalytic activity", these enzymes are typically complex mixtures of biochemical substances. Therefore, these enzymatic reagents are difficult to characterize on a molecular chemical basis and are also difficult to completely purify and isolate. Not infrequently, many of these enzymatic reagents contain undesired amounts of other enzymes, the detection and removal of which involves costly purification and isolation procedures. Accordingly, in many cases, addition of an "inhibitor" to eliminate or substantially reduce unwanted enzymatic activity in a particular liquid analysis procedure employing an enzymatic reagent can be much less costly and more convenient. The inhibitor functions to physically or chemically block or at least substantially reduce the enzymatic activity of the undesired enzyme.

U.S. Pat. No. 3,956,069 issued May 11, 1976 discloses enzymatic assays for determining the presence or concentration of several different serum analytes including glucose and creatine phosphokinase by use of nicotinamide adenine dinucleotide (NAD) or the reduced form of nicotinamide adenine dinucleotide (NADH). The patent discloses that the enzyme lactate dehydrogenase (LDH) interferes with these enzymatic assays because of the following reaction which is catalyzed by LDH:

As shown in the above-identified reaction, if there is any lactate or lactic acid (lactic acid being converted to its lactate form at any pH greater than about 5), the presence of the enzyme LDH may cause the lactate to interfere with the assay. That is, LDH, due to its activity on lactate, can also catalyze conversion of NAD to NADH and thereby contribute a source of error to an enzymatic assay which is based on the NAD-NADH reaction couple. To eliminate the source of this interference, U.S. Pat. No. 3,956,069 discloses that oxalic acid, oxamic acid, or their salts, can be added to the enzymatic reagent to inhibit the action of the LDH enzyme on lactate.

U.S. Pat. No. 3,956,069 describes no method for the inhibition of the enzyme lactate oxidase. The presence of lactate oxidase in an enzymatic reagent can provide a major interferent in many liquid analysis procedures in which lactate or lactic acid is also present. This is because many liquid analysis procedures employ an enzymatic reaction sequence in which hydrogen peroxide is produced and because lactate oxidase catalyzes the following reaction:

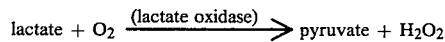

Thus, enzymatic, "hydrogen peroxide-linked" liquid analyses, i.e., those anlayses that determine the presence or concentration of a selected analyte by an enzymatic reaction sequence in which hydrogen peroxide is produced, can clearly be interferred with by the action of any lactate oxidase present in the enzymatic reagent whenever these analyses are performed on aqueous liquids containing, in addition to the selected analyte, lactate or lactic acid. Lactate or lactic acid is generally present in serum and whole blood, and therefore will produce interference in enzymatic hydrogen peroxide-linked assays performed on serum or whole blood samples using enzymatic reagent compositions containing lactate oxidase in addition to the desired enzymatic reagents. Accordingly, the discovery of an inhibitor for lactate oxidase would represent a highly useful contribution to the art.

SUMMARY OF THE INVENTION

The present invention provides inhibition of lactate oxidase and provides an improved enzymatic analysis of an aqueous liquid that may contain lactate or lactic acid, such analysis being performed for an analyte other than lactate or lactic acid. One embodiment of the invention is directed to those analyses of aqueous liquids wherein the presence or concentration of the desired analyte other than lactate or lactic acid is determined, in whole or in part, by means of an enzymatic reagent composition which produces hydrogen peroxide as a detectable species in the presence of the analyte. In these analyses, lactate or lactic acid, if present in the aqueous liquid, becomes an interferent in the presence of lactate oxidase that may also be present whereby spurious amounts of hydrogen peroxide are produced.

In accordance with the invention, the undesired enzymatic activity of lactate oxidase on any lactic acid and lactate present, for example, in a liquid under analysis, is eliminated or at least substantially reduced by the presence of at least one lactate oxidase inhibitor selected from the group consisting of glycolic acid, oxalic acid, glyoxalic acid, or salts of the foregoing acids. The presence of one or more of the foregoing acids or their salts has been found effective to completely block or at least substantially reduce the undesired enzymatic activity of lactate oxidase.

In one embodiment, the invention provides a method for inhibition of lactate oxidase which comprises interacting lactate oxidase and at least one of the above-named inhibitors to reduce the activity of the lactate oxidase on lactic acid and lactate.

A preferred embodiment of the invention provides an improved method for inhibiting the enzymatic activity of lactate oxidase in an enzymatic reagent composition containing lactate oxidase, one or more other selected enzyme(s) effective to generate $H_2O_2$ in the presence of oxygen and substrate for the enzyme(s) other than lactate or lactic acid. This is accomplished by adding to the reagent composition, at least one of the above-named inhibitors. The resultant enzymatic composition, even though containing sufficient lactate oxidase to generate hydrogen peroxide in the presence of oxygen and lactic acid or lactate and cause interference with the other components of the enzymatic reagent composition, exhibits little or no lactate oxidase activity due to the presence of the inhibitor.

A further embodiment of the invention provides an enzymatic reagent composition comprising one or more enzyme(s) effective to generate hydrogen peroxide in the presence of oxygen and substrate for the enzyme(s) other than lactic acid or lactate, and at least one of the above-identified lactate oxidase inhibitors, namely, glycolic acid, oxalic acid, glyoxalic acid, or a salt thereof.

The present invention is particularly useful in an enzymatic method and an enzymatic reagent composition for the analysis of an aqueous biological liquid such as serum, blood, or urine, wherein the enzymatic method and reagent composition employ an enzymatic reagent comprising L-α-glycerophosphate oxidase (α-GPO) and a reagent exhibiting peroxidative activity, e.g., peroxidase. α-GPO interacts with L-α-glycerophosphate, a decomposition product produced by various serum components such as glycerol, triglycerides, adenosine triphosphate (ATP), and the like, in the presence of oxygen to produce hydrogen peroxide which, in the presence of the reagent having peroxidative activity, can be interacted with a hydrogen peroxide detector to produce a detectable change.

Because α-GPO is often contaminated with lactate oxidase, and because aqueous biological fluids such as serum typically contain lactic acid or lactate as a component thereof, analysis of serum for analytes other than lactic acid or lactate by use of an enzymatic, hydrogen peroxide-linked reagent composition employing α-GPO contaminated by lactate oxidase will result in the production of spurious hydrogen peroxide, thereby leading to assay error. To eliminate this source of error one could further purify the α-GPO-containing enzymatic reagent composition to remove the lactate oxidase contaminant. The present invention, however, provides a considerably less expensive and a much more convenient means to achieve the same result; namely elimination or reduction of any undesired lactate oxidase activity by use of a lactate oxidase inhibitor.

DESCRIPTION OF THE PREFERRED EMBODIMENT

The present invention features the use of an inhibitor for lactate oxidase. The inhibitor represents one or more components selected from the group consisting of glycolic acid, oxalic acid, glyoxalic acid, and salts thereof. Both the acid and salt forms of these inhibitors are useful. When the salt form of these inhibitors is used, the selection of a particular salt, e.g., an alkali metal, ammonium, or alkaline earth metal salt, is not critical; any of the known salt forms of these inhibitors are generally considered to be useful. The use of one or more of the aforementioned inhibitors is essential to the present invention. A variety of closely related chemical homologues and analogues of the aforementioned inhibitors have been tested to discover additional inhibitors, but the results of these tests have demonstrated that these chemical homologues and analogues are ineffective as inhibitors for lactate oxidase. Thus, glycine, lactamide, methoxyacetic acid, malic acid, α-ketoglutaric acid, and β-hydroxybutyric acid have each been tested and found to provide little or no inhibition of lactate oxidase activity. Similarly, compounds such as oxamic acid, oxamide, malonic acid, glyceric acid, α-hydroxybutyric acid have been tested as inhibitors and, although capable of producing some inhibition of lactate oxidase, each of these compounds has been found ineffective to produce 50% or more inhibition of the enzymatic activity of lactate oxidase, as measured at 30° C.

Based on the above-noted tests relating to the lack of inhibition provided by many of the chemical analogues and homologues of the lactate oxidase inhibitors employed in the present invention, the action of these inhibitors is considered quite unique.

The lactate oxidase activity inhibited by the present invention is the activity of those lactate oxidases which, in the presence of oxygen, can convert lactic acid or lactate to pyruvate and hydrogen peroxide. These lactate oxidases should be distinguished from those oxidases which are known to catalyze the reaction of lactic acid or lactate in the presence of oxygen to produce acetate, carbon dioxide, and water. Examples of those oxidases which catalyze a reaction producing water, rather than hydrogen peroxide, and which are therefore outside the scope of the present invention are reported by Sutton in *Journal Of Biological Chemistry*, Vol. 226, page 395 (1957). Those oxidases outside the scope of the present invention have recently been renamed lactate 2-monooxygenase and renumbered as International Enzyme Number 1.13.12.4. See *Enzyme Nomenclature Recommendations* (1972) of the International Union of Pure and Applied Chemistry and the International Union of Biochemistry, Elsevier Scientific Publishing Co., page 62, 108, 109, 346, and 376, reprinted 1975.

Two known sources for lactate oxidase within the scope of the present invention, i.e., an oxidase which in the presence of oxygen converts lactate or lactic acid to pyruvate and hydrogen peroxide, are *Tetrahymena pyriformis* as reported by Eichel et al, "Respiratory Enzyme Studies in Tetrahymena Pyriformis", *Journal of Biological Chemistry*, Vol. 237, No. 3, page 940 (1962) and preferably *Streptococcus faecium* (formerly called *Streptotoccus faecalis*) as described in U.S. Pat. No. 4,166,763 issued Sept. 4, 1979.

Because *Streptococcus faecium* is a particularly useful microbial source for other oxidase enzymes, such as α-GPO which can advantageously be employed in the enzymatic assay of serum triglycerides, the preferred lactate oxidase inhibitors of the present invention are those which can be used with other hydrogen peroxide-generating oxidases derived from *Streptotoccus faecium*. The preferred lactate oxidase inhibitors include glycolic acid, oxalic acid, and their salts. When used together with other hydrogen peroxide-generating oxidase enzymes derived from *Streptotoccus faecium*, these preferred inhibitors of the present invention eliminate or at least substantially reduce any contaminating lactate oxidase activity which is typically present in these enzyme preparations but do not inhibit the activity of the desired oxidase, e.g., α-GPO. Thus, by use of the present invention, one can employ these other hydrogen peroxide-generating oxidase enzymes derived from *Streptotoccus faecium* without extensive purification and isolation procedures to eliminate the undesired lactate oxidase activity present in these enzyme preparations.

For example, *Research Disclosure* (published by Industrial Opportunities, Ltd.; Homewell, Havant; Hampshire, PO9 1EF, U.K.) Publication No. 16146, Volume 161, published on Sept. 10, 1977, describes an enzymatic analysis method and reagent composition for the quantification of glycerol or triglycerides contained in aqueous liquid such as blood serum. In this enzymatic assay, an enzymatic reagent composition is employed to convert serum triglyceride to glycerol, the glycerol is then converted to L-α-glycerophosphate which, in turn, is enzymatically oxidized by use of the enzyme α-GPO to produce detectable quantities of hydrogen peroxide. The preferred α-GPO employed in the foregoing enzymatic assay is derived from the aforementioned *Streptococcus faecium* microbial source. Because this same microbial source can provide an extremely effective lactate oxidase as well as the aforementioned α-GPO, removal of the lactate oxidase activity from any α-GPO derived from *Streptococcus faecium* is extremely important.

If the lactate oxidase activity which is present in α-GPO derived from *Streptotoccus faecium* is not eliminated or substantially reduced, the lactate oxidase activity will interfere with the aforementioned serum glycerol and triglycerides assay because of the lactate constituent also present in serum. This leads to the production of spurious amounts of hydrogen peroxide, thereby representing a source of error in the aforementioned serum glycerol or serum triglycerides assay. Use of the preferred lactate oxidase inhibitors of the present invention effectively eliminates this source of assay error in the above-referenced serum glycerol and triglycerides assay without affecting the activity of the α-GPO.

The amount of lactate oxidase inhibitor employed in a particular analysis and reagent composition will depend upon a number of factors, including the undesired lactate oxidase activity of the enzymatic composition, the amount of lactate contained in the liquid sample to be analyzed, the concentration of the desired analyte in the liquid sample under analysis, and the hydrogen peroxide-generating activity of the other oxidase enzyme components of the enzymatic reagent composition. For example, where the serum analyte under investigation is present in relatively low concentration (as is often the case) or where the lactic acid or lactate component of the liquid under analysis is present in relatively high concentration compared to the concentration of the desired analyte, or where the enzymatic activity of the lactate oxidase in the enzymatic reagent composition is relatively high compared to the desired activity of the other hydrogen peroxide-generating oxidase of the reagent composition, the use of larger amounts of the lactate oxidase inhibitor(s) of the present invention becomes extremely advantageous.

Ordinarily, it is desirable to use the inhibitors defined herein only in those instances where lactate oxidase and lactate or lactic acid are expected to be present together. That is, if either the lactate oxidase enzyme or its lactate substrate are certain to be absent, the inhibitor in theory can be dispensed with. However, in practice such certainty entails a potentially expensive and time-consuming analytical assessment of the enzymatic reagent composition for lactate oxidase and of liquid samples for lactate substrate. It is an advantage of the present invention, therefore, that an enzymatic reagent composition for the generation of hydrogen peroxide—and an enzymatic analysis using such composition—comprises the lactate oxidase inhibitor without regard to the presence of lactate oxidase in the composition or the presence of lactate substrate in the liquid under analysis. Accordingly, the inhibitor serves not only to inhibit when lactate oxidase and substrate are brought together, but also as an assurance against their possible presence even though lactate oxidase or its substrate may be absent. The state of the art is thus advanced by providing certainty against lactate interference and dispensing with the need to assay for the presence of the interfering substances.

In a typical liquid analysis procedure for serum glycerol or triglycerides employing the above described enzymatic assay using the hydrogen peroxide generating enzyme α-GPO obtained from *Streptococcus faecium*, the amount of lactate oxidase inhibitor employed in such an enzymatic assay composition is typically within the range of from about 5 to about 50 millimolar concentration.

In addition to the above described serum glycerol and serum triglycerides enzymatic reagent compositions containing α-GPO, the lactate oxidase inhibitors of the present invention can advantageously be incorporated in a number of other hydrogen peroxide-generating, oxidase-containing enzymatic reagent compositions. For example, the lactate oxidase inhibitors of the invention can be admixed in an enzymatic reagent composition containing glucose oxidase for determination of serum glucose. Similarly, these inhibitors can be employed in an enzymatic reagent composition containing cholesterol oxidase for determination of serum cholesterol, or in a composition containing uricase for analysis of uric acid.

The "interaction" of the lactate oxidase inhibitors with lactate oxidase is accomplished by contacting together the desired inhibitor and lactate oxidase under conditions at which the lactate oxidase would otherwise be expected to be quite active. Preferably, this interaction takes place in the presence of an aqueous medium at a pH within the range of from about 5.5 to 9.5 and a temperature of from about 20° to 45° C., although in certain applications other pH and temperature conditions may be useful. Similarly, "interaction" of an enzymatic reagent composition with the desired analyte in the presence of the lactate oxidase inhibitor described herein takes place under pH and temperature conditions, such as those noted immediately hereinabove, at which the various components of the enzymatic reagent composition and lactate oxidase are normally quite effective. The lactate oxidase inhibitor effectively reduces or blocks the lactate oxidase activity, if any, but preferably does not adversely interfere with the activity of the other components of the enzymatic reagent composition on the desired analyte.

The enzymatic analysis method and reagent composition of the invention for inhibition of undesired lactate oxidase activity can be employed in liquid analytical techniques. These are sometimes called "wet chemistry" techniques. The analysis method and reagent compositions can also be employed in assays employing "dry chemistry" techniques.

In "wet chemistry" techniques, the assay is carried out entirely in a liquid medium. The enzymatic reagent composition can be added to the liquid medium either as a dried reagent or as a liquid reagent. The lactate oxidase inhibitor can advantageously be admixed in the liquid assay medium together with the other components of the enzymatic reagent composition or it can be added separately to the liquid assay medium.

As noted above, an enzymatic reagent composition containing the lactate oxidase inhibitor can be prepared and used as a liquid reagent, e.g., in aqueous liquid form, or as a dried reagent, e.g., as a freeze-dried powder. The dried reagent can be packaged and stored and later reconstituted with water immediately prior to use.

When the enzymatic analysis method and reagent composition of the invention are employed in "dry chemistry" techniques, the composition containing the lactate oxidase inhibitor can be incorporated, for example, by imbibition, impregnation, or by coating techniques, into a reagent zone of an essentially dry (i.e., dry-to-the-touch) analytical element, e.g., a reagent layer of a dip-and-read fibrous test strip or a reagent layer of a non-fibrous, multilayer analytical element as described in Przybylowicz et al, U.S. Pat. No. 3,992,158 and Goffe et al U.S. Pat. No. 4,042,335.

In "dry chemistry" test elements, the enzymatic reagent composition containing the lactate oxidase inhibitor is present as a dried reagent. As described in U.S. Pat. No. 3,992,158 noted above, multilayer dry chemistry analytical elements can include more than one reagent layer, each of the individual reagent layers being in fluid contact with one another under conditions of use of the element, i.e., upon application of a liquid sample onto the analytical element for analysis thereof. In such case, each of the various components of an enzymatic reagent composition contained in such multilayer analytical elements can be located in each of the separate reagent layers, or some of the reagent components can be located in one layer while other reagent components are located in a different layer.

The examples below further illustrate the invention. In the examples, the following materials were used:

MATERIALS

A. The following materials were obtained from Sigma Chemical Co., St. Louis, Mo.: lactamide, DL-glyceric acid, α- and β-hydroxybutyric acids, DL-α-glycerophosphate, L-lactic acid, horseradish peroxidase, and orthodianisidine.

B. The following were obtained from Aldrich, Metuchen, N.J.: tartronic acid and oxamic acid.

C. Most of the remaining materials noted in the examples were obtained from Eastman Organic Chemicals, Eastman Kodak Co., Rochester, N.Y.

In the examples, oxidative enzymes were prepared from *Streptococcus faecium* ATCC 12755. L-lactate oxidase was isolated from *Streptococcus faecium* as a 0–50% ammonium sulfate fraction as described in Esders et al., U.S. Pat. No. 4,166,763 issued Sept. 4, 1979. L-α-glycerophosphate oxidase was purified from *Streptococcus faecium* as described in Table V, of *Research Disclosure* Publication No. 16146 published Sept. 10, 1977. Extensively purified L-α-glycerophosphate oxidase (material carried through the whole purification sequence) contained L-α-glycerophosphate:lactate oxidase activity ratios of (1700–3000:1), whereas the partially purified L-α-glycerophosphate oxidase (material isolated as the 50–80% ammonium sulfate fraction) contained L-α-glycerophosphate:lactate oxidase activity ratios of 30–100:1.

In the examples, enzyme assays for lactate oxidase were carried out as follows: Assay reaction mixtures contained in a total volume of 1.0 ml: 100 μmoles potassium phosphate buffer, pH 7.0, 25 μmoles lactic acid, 25 mg horseradish peroxidase (4.6 purpurogallin units), and 0.25 μmoles orthodianisidine. Compounds to be tested as potential inhibitors for lactate oxidase were added to the assay reaction mixtures as indicated in Example 1. Samples were equilibrated at 30° C. and then reactions were initiated by addition of *Streptococcus faecium* lactate oxidase. Absorbance at 430 nm was measured in a Beckman 25 spectrophotometer. Initial rates were calculated from the linear portion of the curve.

In the examples, enzyme assays for L-α-glycerophosphate oxidase were carried out as follows: Assay reaction mixtures contained in a total volume of 1.0 ml: 100 μmoles potassium phosphate buffer, pH 7.0, 66 μg orthodianisidine, 25 μg horseradish peroxidase (4.6 purpuragallin units) and 200 μmoles DL-α-glycerophosphate (at pH 7.0). Compounds to be tested as potential inhibitors were added to the reaction mixtures as indicated in Example 1. Samples were equilibrated at 37° C. and the reactions were initiated by the addition of an aliquot of enzyme. Absorbance at 430 nm was measured in a Beckman 25 spectrophotometer. Initial rates were calculated from the linear portion of the curve.

In the examples, non-fibrous, multilayer, "dry chemistry" analytical elements for determination of serum triglycerides were formulated having the following structure and composition:

---

Non-fibrous, isotropically porous spreading layer composition containing "blushed" cellulose acetate; non-ionic surfactant; and $TiO_2$ as described in U.S. Pat. Nos. 3,992,158 and 4,042,335

Polymeric Subbing Layer

Hydrolysis layer composition containing lipase derived from *Candida rugose* and non-ionic surfactant as described in U.S. Pat. No. 4,179,334 issued December 18, 1979

Buffered-gelatin layer composition containing deionized gelatin; gel hardener; plasticizer; 0.05M potassium phosphate buffer, pH 7.0; and non-ionic surfactant Enzymatic reagent layer composition Poly(ethylene terephthalate) film support

---

The enzymatic reagent layer composition of the above-noted "dry chemistry" analytical element contained deionized gelatin (5.4 g/m$^2$); gel hardener (32.4 mg/m$^2$); poly(methyl acrylate-co-2-acrylamido-2-methylpropanesulfonic acid-co-2-acetoacetoxyethyl methacrylate) having a monomer weight ratio of (88.8:4.7:6.5) as peroxidase stabilizer (5.4 g/m$^2$); 0.05 M potassium phosphate buffer, pH 7.0; Triton X-100 surfactant (389 mg/m$^2$); 2-(3,5-dimethoxy-4-hydroxyphenyl)4,5-bis(4-dimethylaminophenyl)imidazole as a leuco dye (405 mg/m$^2$ dispersed in 2,4-di-n-amylphenol (4.05 g/m$^2$); antioxidant (324 mg/m$^2$); MgCl (103 mg/m$^2$); adenosinetriphosphate (1.35 g/m$^2$); peroxidase (7020 U/m$^2$); glycerol kinase (324 U/m$^2$); and either purified or partially purified L-α-glycerophosphate oxidase (2840 U/m$^2$). When the partially purified L-α-glycerophosphate oxidase was used, glycolate was incorporated into that layer in the amounts noted below in Example 2.

EXAMPLE 1

Selective Inhibition of L-Lactate Oxidase Obtained From *Streptococcus faecium*

To find a compound which would selectively inhibit L-lactate oxidase, even in the presence of other enzymes from the same source, such as L-α-glycerophosphate oxidase, several compounds were added to reaction mixtures and the enzymes were assayed as described above. As can be seen in Table I, oxalic and glycolic acids greatly inhibit the L-lactate oxidase. Glyoxalic acid also inhibited the enzyme, and it inhibited L-α-GPO as well.

TABLE I

Selective Inhibition of L-Lactate Oxidase Obtained from *Streptococcus faecium* ATCC 12755

Each compound was added to the reaction mixtures at a concentration of 5 mM. The rate of reaction in the absence of compound was considered 100%, and the percent inhibition of reaction due to each compound was calculated accordingly.

| Compound | L-Lactate Oxidase | L-α-Glycerophosphate Oxidase |
|---|---|---|
| | Percent Inhibition | |
| None | 0 | 0 |
| Glyoxalic Acid | 100 | 100 |
| Oxalic Acid | 94 | 0 |
| Glycolic Acid | 90 | 0 |
| Oxamic Acid | 40 | — |
| Oxamide | 43 | — |
| Methoxyacetic Acid | 0 | — |
| Glycine | 0 | — |
| Lactamide | 0 | — |
| Tartronic Acid | 10 | — |
| Malonic Acid | 30 | — |
| Glyceric Acid | 21 | — |
| α-Hydroxybutyric Acid | 7 | — |
| β-Hydroxybutyric Acid | 0 | — |
| Malic Acid | 0 | — |
| α-Ketoglutaric Acid | 0 | — |

EXAMPLE 2

Reduction of Lactate Blank Reaction by Glycolic Acid

A. Dry Chemistry Test Element Mode: Dry chemistry analytical elements for the determination of triglycerides were prepared with either the purified or partially purified L-α-GPO as described above. Glycolate was added to the elements as indicated in Table II. To each element, a 10 μl sample of DL-lactate (20 mg/dl) was applied and the reflection density of the element, $D_R$, at 540 nm was measured through the element support after a seven-minute incubation at 37° C. The reduction of the lactate blank reaction in the presence of glycolate as the inhibitor is shown in Table II. In the absence of the inhibitor, the partially purified preparation produced a higher response to lactate (3.4 times control), but at 81 mg/m$^2$ glycolic acid, the blank was substantially lowered (1.6 times control), and at 405 mg/m$^2$ glycolic acid, reaction with lactate was less than that observed with the purified L-α-glycerophosphate oxidase (control).

TABLE II

Reduction of Lactate Blank Reaction by Glycolic Acid

| Enzyme | Response to Lactate ($D_R$) |
|---|---|
| Purified L-α-Glycerophosphate Oxidase (control) | 0.025 |
| Partially Purified L-α-Glycero-Phosphate Oxidase | 0.086 |
| plus 81 mg/m$^2$ Glycolic Acid | 0.04 |
| plus 405 mg/m$^2$ Glycolic Acid | 0.01 |

B. Solution Mode: The reduction of serum blank by the addition of glycolate, even in the presence of elevated amounts of lactate, was demonstrated in a solution system containing partially purified DL-α-glycerophosphate oxidase as follows:

Solution incubation mixtures contained in a total volume of 1.0 ml: 100 μmoles potassium phosphate buffer, pH 7.0, 0.12 mg 4-aminoantipyrene.HCl, 0.04 mg 1,7-dihydroxynaphthalene, 25 μg horseradish peroxidase (4.6 purpurogallin units), 0.36 units glycerol kinase, 4.6 units partially purified DL-α-glycerophosphate oxidase, and 10 mg Triton X-100. Reactions were initiated by addition of 20 μl of normal serum or 50 μl of 1 mM Dl-lactate, and after ten minutes at 37° C., the absorbance was measured at 490 nm. In each case, a reagent blank (all components except substrate) was subtracted to give the change in absorbance at 490 nm, $\Delta A_{490}$.

Table III shows the reduction in blank reactions obtained by the addition of glycolate using both normal serum and 50 μl of 1 mM DL-lactate as substrates.

TABLE III

Reduction of Lactate Blank Reaction by Glycolic Acid - Solution Mode

| Glycolate | Response to Normal Serum $\Delta A_{490}$ | Response to 50 μM DL-Lactate $\Delta A_{490}$ |
|---|---|---|
| None | 0.074 | 0.029 |
| 1 mM | 0.006 | 0.008 |
| 2 mM | 0 | 0 |
| 3 mM | 0 | 0 |

EXAMPLE 3

Comparison of Dry Chemistry Triglyceride Test Element Containing Purified L-α-Glycerophosphate Oxidase to that Containing Partially Purified Enzyme Plus Glycolate Dry chemistry analytical elements (as described above) containing purified L-α-glycerophosphate oxidase and partially purified enzyme plus two different levels of glycolate were compared for response to serum triglycerides and glycerol. One set of analytical elements contained 2840 U/m$^2$ purified L-α-glycerophosphate oxidase; two other sets of elements contained 2840 U/m$^2$ partially purified L-α-glycerophosphate oxidase and 81 mg/m$^2$ or 405 mg/m$^2$ of glycolate, respectively. Test fluids were three serum-based calibrators containing low triglyceride concentration (I), normal triglyceride concentration (II), high triglyceride concentration (III) and normal serum. A 10 μl sample of test fluid was applied to each element. After a sevenminute incubation at 37° C., the reflection density, $D_R$, at 540 nm was measured through the element support. Results represent the average of duplicates. As can be seen in Table IV, Column A, all three elements produced similar responses when tested with three serum-based triglyceride calibrators and with a normal serum sample. Thus, although glycolate effectively decreased the lactate blank reaction (Example 2), it did not inhibit any of the components of the triglyceride detection system.

TABLE IV

Comparison of Coated Triglyceride Systems Containing Purified
L-α-Glycerophosphate Oxidase to that Containing Partially
Purified Enzyme Plus Glycolate

| | Response($D_R$) | | | | | |
|---|---|---|---|---|---|---|
| | Purified α-GPO | | Partially Purified α-GPO Plus 81 mg/m² Glycolate | | Partially Purified α-GPO Plus 405 mg/m² Glycolate | |
| | | | $D_{R540}$ 7-Minutes | | | |
| Test Fluids | A | B | A | B | A | B |
| Calibrator I | 0.151 | (0.217) | 0.149 | (0.251) | 0.140 | (0.178) |
| Calibrator II | 0.656 | (0.536) | 0.644 | (0.751) | 0.620 | (0.706) |
| Calibrator III | 1.104 | (0.597) | 1.077 | (1.170) | 1.071 | (1.117) |
| Normal Serum | 0.638 | | 0.639 | | 0.625 | |
| Glycerol (5 mM) | | (0.546) | | (1.181) | | (1.131) |

EXAMPLE 4

Effect of Glycolate on Stability of Dry Chemistry Test Elements

The three sets of elements tested in Example 3 were stored at 78° F., 50% RH for four weeks and retested. As shown in Table IV, Column B, the elements containing partially purified enzyme and glycolic acid showed no decrease in response to test fluids after storage at 78° F. and 50% RH for four weeks, whereas the elements containing purified L-α-glycerophosphate oxidase showed decreased response. This was especially evident with calibrator III, a high triglyceride content material and with 5 mM glycerol.

EXAMPLE 5

To demonstrate that the enzymes lactate dehydrogenase (LDH) and L-lactate oxidase (LO) act uniquely and that inhibitors for LO cannot be selected on the basis of the inhibition produced by a specific compound on LDH, the inhibition effect of oxalic, glycolic, and glyoxalic acids on LO and LDH were compared. The effect of these acids on LO was evaluated by studying an LO assay reaction mixture having the composition described above. The effect of these acids on LDH was evaluated by studying an LDH assay reaction mixture which contained in a total volume of 1.0 ml: 50 μmoles potassium phosphate buffer (pH 7.5); 1 μmole sodium pyruvate; 0.13 μmole NADH; 0.02 μg beef meat lactate dehydrogenase (320 U/mg) and the acid at a concentration of 10 mM. In the absence of acid, the rate of reaction was assumed to be 100% and the percent inhibition of each reaction was calculated accordingly. The results as shown in Table V clearly demonstrate that one cannot predict a compound will be an inhibitor for LO on the basis of whether or not the compound inhibits LDH.

TABLE V

| Acid (Concentration) | LO % Inhibition | LDH % Inhibition |
|---|---|---|
| None | 0 | 0 |
| Glyoxalic acid (10mM) | 100 | 15 |
| Oxalic acid (10mM) | 94 | 100 |
| Glycolic acid (10mM) | 90 | 11 |

The invention has been described in detail with particular reference to certain preferred embodiments thereof, but it will be understood that variations and modifications can be effected within the spirit and scope of the invention.

What is claimed is:

1. A method for inhibiting the activity of lactate oxidase, which in the presence of oxygen catalyzes the direct conversion of lactic acid or lactate to pyruvate and hydrogen peroxide rather than water, which method comprises interacting said oxidase and at least one inhibitor selected from the group consisting of glyoxalic acid, oxalic acid, glycolic acid, and salts thereof to reduce the activity of said oxidase on lactic acid and lactate.

2. A method for inhibiting the activity of lactate oxidase enzyme in an enzymatic reagent composition, said lactate oxidase enzyme in the presence of oxygen catalyzing the direct conversion of lactic acid or lactate to pyruvate and hydrogen peroxide rather than water, said composition containing one or more additional enzymes effective to generate hydrogen peroxide in the presence of oxygen and substrate for said additional enzymes, said method comprising adding to said reagent composition at least one lactate oxidase inhibitor selected from the group consisting of glyoxalic acid, glycolic acid, oxalic acid and salts thereof.

3. A method for inhibiting the activity of lactate oxidase as defined in claim 2 wherein said enzymatic reagent composition contains α-glycerophosphate oxidase as one of said additional enzymes and said inhibitor is oxalic acid, glycolic acid, or a salt thereof.

4. A method for inhibiting the activity of lactate oxidase as defined in claim 2 wherein said enzymatic reagent composition contains α-glycerophosphate oxidase derived from *Streptococcus faecium* as one of said additional enzymes, and peroxidase; and said inhibitor is oxalic acid, glycolic acid or salt thereof.

5. A method for the enzymatic analysis of an aqueous liquid wherein said analysis is for the determination of an analyte, other than lactate or lactic acid, using an enzymatic reagent composition which produces hydrogen peroxide as a detectable species in the presence of said analyte, said method comprising detecting said analyte in the presence of at least one inhibitor for lactate oxidase, said lactate oxidase in the presence of oxygen catalyzing the direct conversion of lactic acid or lactate to pyruvate and hydrogen peroxide rather than water, said inhibitor being selected from the group consisting of glycolic acid, oxalic acid, glyoxalic acid and salts thereof.

6. A method for the enzymatic analysis of an aqueous liquid as defined in claim 5 wherein said enzymatic reagent composition comprises α-glycerophosphate oxidase and said inhibitor is selected from the group consisting of oxalic acid, glycolic acid, and salts thereof.

7. A method for the enzymatic analysis of an aqueous liquid as defined in claim 5 wherein said enzymatic reagent composition comprises α-glycerophosphate oxidase derived from *Streptococcus faecium*, peroxidase, and said inhibitor is selected from the group consisting of oxalic acid, glycolic acid, and salts thereof.

8. An enzymatic reagent composition comprising one or more enzymes effective to generate hydrogen peroxide in the presence of oxygen and substrate other than lactate oxidase, said lactate oxidase in the presence of oxygen catalyzing the direct conversion of lactic acid or lactate to pyruvate and hydrogen peroxide rather than water, said inhibitor being selected from the group consisting of glycolic acid, oxalic acid, glyoxalic acid and salts thereof.

9. An enzymatic reagent composition as defined in claim 8 wherein α-glycerophosphate oxidase is one of said enzymes and said inhibitor is oxalic acid, glycolic acid, or a salt thereof.

10. An enzymatic reagent composition as defined in claim 8 wherein one of said enzymes is α-glycerophosphate oxidase derived from *Streptococcus faecium*, said composition contains peroxidase, and said inhibitor is oxalic acid, glycolic acid, or a salt thereof.

11. An essentially dry analytical element comprising an enzymatic reagent composition in one or more reagent zones of said element, each component of said composition being in at least one of said reagent zones, said composition comprising one or more enzymes effective to generate hydrogen peroxide in the presence of oxygen and substrate other than lactate or lactic acid for said enzymes, and an inhibitor for lactate oxidase, said lactate oxidase in the presence of oxygen catalyzing the direct conversion of lactic acid or lactate to pyruvate and hydrogen peroxide rather than water, said inhibitor being selected from the group consisting of glycolic acid, oxalic acid, glyoxalic acid and salts thereof.

12. An essentially dry analytical element as defined in claim 11 wherein α-glycerophosphate oxidase is one of said enzymes and said inhibitor is oxalic acid, glycolic acid, or a salt thereof.

13. An essentially dry analytical element as defined in claim 11 wherein one of said enzymes is α-glycerophosphate oxidase derived from *Streptococcus faecium*, said enzymatic reagent composition contains peroxidase, and said inhibitor is oxalic acid, glycolic acid, or a salt thereof.

* * * * *